US010274497B2

United States Patent
Lee et al.

(10) Patent No.: US 10,274,497 B2
(45) Date of Patent: Apr. 30, 2019

(54) APTAMER SPECIFIC TO OVARIAN CANCER AND DETECTION METHOD FOR OVARIAN CANCER

(71) Applicant: National Tsing Hua University, Hsinchu (TW)

(72) Inventors: Gwo-Bin Lee, Hsinchu (TW); Lien-Yu Hung, Hsinchu (TW); Chih-Hung Wang, Hsinchu (TW); Chien-Yu Fu, Hsinchu (TW); Wen-Bin Lee, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/424,896

(22) Filed: Feb. 6, 2017

(65) Prior Publication Data

US 2018/0136217 A1    May 17, 2018

(30) Foreign Application Priority Data

Nov. 17, 2016  (TW) .............................. 105137598 A

(51) Int. Cl.
  *C12N 15/115*  (2010.01)
  *G01N 33/574*  (2006.01)

(52) U.S. Cl.
  CPC ..... *G01N 33/57449* (2013.01); *C12N 15/115* (2013.01)

(58) Field of Classification Search
  None
  See application file for complete search history.

(56) References Cited

U.S. PATENT DOCUMENTS

| 8,039,609 | B2 | 10/2011 | Missailidis et al. | |
|---|---|---|---|---|
| 2007/0065844 | A1* | 3/2007 | Golub | C12Q 1/6834 435/6.14 |

FOREIGN PATENT DOCUMENTS

| CN | 104988154 | 10/2015 |
|---|---|---|
| TW | 201604281 | 2/2016 |
| TW | 201608023 | 3/2016 |

OTHER PUBLICATIONS

Pobanz et al (Methods 106 (2016) 14-20) (Year: 2016).*
Wang et al. "Cancer Cell-Specific Oligopeptides Selected by an Integrated Microfluidic System from a Phage Display Library for Ovarian Cancer Diagnosis", Theranostics, Feb. 5, 2015, pp. 431-442.
Hung et al., "Screening of aptamers specific to colorectal cancer cells and stem cells by utilizing On-chip Cell-SELEX", scientific reports, May 22, 2015, pp. 1-12.
Hung et al., "An on-chip Cell-SELEX process for automatic selection of high-affinity aptamers specific to different histologically classified ovarian cancer cells", The Royal Society of Chemistry, Aug. 6, 2014, pp. 1-12.
Che et al., "An integrated microfluidic system for screening of phage-displayed peptides specific to colon cancer cells and colon cancer stem cells", Biomicrofluidics 9, Oct. 15, 2015, pp. 1-15.
Lien-Yu Hung et al.,"Development of Specific Aptamers With Different Histological Classified Ovarian Cancer Cells by Utilizing On-Chip OVCA Cell-SELEX", 17th International Conference on Miniaturized Systems for Chemistry and Life Sciences, Oct. 27-31, 2013, pp. 368-370.
Seyedeh Alia Moosavian, et al.,"Development of RNA aptamers as molecular probes for HER2+ breast cancer study using cell-SELEX", Iran J Basic Med Sci., vol. 18, No. 6, Jun. 2015, pp. 576-586.

* cited by examiner

*Primary Examiner* — Richard A Schnizer
(74) *Attorney, Agent, or Firm* — JCIPRNET

(57) ABSTRACT

An aptamer specific to ovarian cancer and a detection method for ovarian cancer are provided. The aptamer includes a following nucleotide sequence: 5'-ncaaannncnnn-nanncnnnnnnnnnnngaannnannngg-3', wherein n is a nucleotide independently selected from "a," "t," "c," and "g."

8 Claims, 5 Drawing Sheets
(3 of 5 Drawing Sheet(s) Filed in Color)
Specification includes a Sequence Listing.

the aptamer A          the aptamer B

SEQUENCE LISTING

```
<160> NUMBER OF SEQ ID NOS: 6

<210> SEQ ID NO 1
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(28)
<223> OTHER INFORMATION: n is a, c, g, or t
<220> FEATURE:
<221> NAME/KEY: misc_feature
<222> LOCATION: (32)..(34)
<223> OTHER INFORMATION: n is a, c, g, or t
<220> FEATURE:
<221> NAME/KEY: misc_feature
<222> LOCATION: (36)..(38)
<223> OTHER INFORMATION: n is a, c, g, or t

<400> SEQUENCE: 1
ncaaannncn nnnanncnnn nnnnnnnnga annnannngg                                 40
```

```
<210> SEQ ID NO 2
<211> LENGTH: 40
<212> TYPE: DNA
<213> ORGANISM: Artificial Sequence
<220> FEATURE:
<223> OTHER INFORMATION: Synthetic

<400> SEQUENCE: 2
tcaaattacg gaaaatcatg acggggtgga accgaggggg                              40

<210> SEQ ID NO 3
<211> LENGTH: 40
<212> TYPE: DNA
<213> ORGANISM: Artificial Sequence
<220> FEATURE:
<223> OTHER INFORMATION: Synthetic

<400> SEQUENCE: 3
gcaaacagct ctgagacgaa ttccatgtga aaacattcgg                              40

<210> SEQ ID NO 4
<211> LENGTH: 72
<212> TYPE: DNA
<213> ORGANISM: Artificial Sequence
<220> FEATURE:
<223> OTHER INFORMATION: Synthetic

<400> SEQUENCE: 4
acagcaccac agaccatcaa attacggaaa atcatgacgg ggtggaaccg aggggggtgtt       60 tgtcttcctg cc                                                           72

<210> SEQ ID NO 5
<211> LENGTH: 72
<212> TYPE: DNA
<213> ORGANISM: Artificial Sequence
<220> FEATURE:
<223> OTHER INFORMATION: Synthetic

<400> SEQUENCE: 5
acagcaccac agaccagcaa acagctctga gacgaattcc atgtgaaaac attcggtgtt        60
tgtcttcctg cc                                                           72

<210> SEQ ID NO 6
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(56)
<223> OTHER INFORMATION: n is a, c, g, or t

<400> SEQUENCE: 6
ggcaggaaga caaacannnn nnnnnnnnnn nnnnnnnnnn nnnnnnnnnn nnnnnntggt        60
ctgtggtgct gt                                                           72
```

APTAMER SPECIFIC TO OVARIAN CANCER AND DETECTION METHOD FOR OVARIAN CANCER

CROSS-REFERENCE TO RELATED APPLICATION

This application claims the priority benefit of Taiwan application serial no. 105137598, filed on Nov. 17, 2016. The entirety of the above-mentioned patent application is hereby incorporated by reference herein and made a part of this specification.

BACKGROUND OF THE INVENTION

Field of the Invention

The invention relates to an aptamer and a detection method, and particularly relates to an aptamer specific to ovarian cancer and a detection method for ovarian cancer.

Description of Related Art

Ovarian cancer is one of the common gynecological cancers, and the prognosis is usually good with early diagnosis. However, since most of the ovarian cancers at the early stages are not easily to be diagnosed due to inconspicuous symptoms, the cancer usually has already spread and advanced to later stages for most women when a diagnosis of ovarian cancer is confirmed. The average five-year survival rate for late-stage ovarian cancer patients is only 10 to 20% approximately. Ovarian cancer can occur in any age group, and the incidence rate increases with age. Epithelial-stromal tumors primarily occur in women over the age of 40, and malignant germ cell tumors most easily occur in patients less than 20 years of age.

The priority issues in the treatment of malignant tumors are early detection and early diagnosis. As the average life expectancy increases, early diagnosis of cancer is getting more and more attention. However, so far there has not been a detection method that can effectively detect early-stage ovarian cancer. Clinically, common screening methods for ovarian cancer include the following kinds: (1) virginal ultrasonic examination and Doppler ultrasound examination. But since early-stage ovarian cancer is similar to normal ovaries in size and appearance, such ultrasound examination has its difficulty and limitations; (2) serum tumor markers, such as CA-125, Lysophosphatidic acid (LPA), alpha-fetoprotein (A-FP), human chorionic gonadotropin (hCG), inhibin, and Mullerian inhibiting substance (MIS) and so on. Current studies show that the clinical usage of serum tumor markers is primarily for after-surgery follow-up and for early detection of recurrent tumors. However, since such markers have low specificity, it is still necessary to develop other serum tumor markers with high specificity to ovarian cancer for future clinical research and cancer detection so as to facilitate rapid detection of early-stage ovarian cancer and to improve the prognosis and survival rate.

SUMMARY OF THE INVENTION

The invention provides an aptamer specific to ovarian cancer.

The invention provides a detection method for ovarian cancer, and the method has high sensitivity and specificity.

The invention provides an aptamer specific to ovarian cancer. The aptamer includes a following nucleotide sequence: 5'-ncaaannncnnnnanncnnnnnnnnnnngaann-nannngg-3' (SEQ ID NO: 1). Here, n is a nucleotide independently selected from a, t, c, and g.

In one embodiment of the invention, the aptamer includes a following nucleotide sequence: 5'-tcaaattacggaaaatcat-gacggggtggaaccgaggggg-3' (SEQ ID NO: 2).

In one embodiment of the invention, the aptamer includes a following nucleotide sequence: 5'-gcaaacagctctgagacgaat-tccatgtgaaaacattcgg-3' (SEQ ID NO: 3).

In one embodiment of the invention, a variation of the free energy (A G) of the aptamer is, for example, less than −5 kcal/mol.

In one embodiment of the invention, the aptamer, for example, has a stem-loop secondary structure.

In one embodiment of the invention, a 5'-end of the aptamer is modified by any of fluorescence, a thiol group, a biotin, and an enzyme.

The invention provides a detection method for ovarian cancer, and the detection method includes the following steps. First, at least one of the above aptamers is provided. Next, a test sample is mixed with the aptamer to make the test sample bind to the aptamer. Then, the aptamer that binds to the test sample is detected.

In one embodiment of the invention, the test sample, for example, includes an ovarian cancer tissue or an ovarian cancer cell.

In one embodiment of the invention, the ovarian cancer tissue includes a serous ovarian carcinoma tissue, a clear cell ovarian carcinoma tissue, a mucinous ovarian carcinoma tissue, or an endometrioid ovarian carcinoma tissue.

In one embodiment of the invention, the ovarian cancer cell includes OVCAR-3.

Based on the above, the aptamer of the invention has high specificity and affinity to different histologically-classified ovarian cancer tissues and/or ovarian cancer cells. Therefore, a detection method for ovarian cancer using the above aptamer has the advantages of rapid detection, high sensitivity, and high specificity.

To make the aforementioned and other features and advantages of the invention more comprehensible, several embodiments accompanied with drawings are described in detail as follows.

BRIEF DESCRIPTION OF THE DRAWINGS

The disclosure contains at least one color photograph. Copies of the disclosure publication with the color photographs will be provided by the Patent & Trademark Office upon request and payment of the necessary fee. The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

In the invention, an in vitro selection technique of systematic evolution of ligands by exponential enrichment (SELEX) is combined with an integrated microfluidic system to select an aptamer that possesses binding specificity to ovarian cancer, and the aptamer so selected exhibits high binding affinity to different types of ovarian cancer tissues and cells. To make the invention more comprehensible, the selection procedure of the aptamer is described in detail in the following embodiments.

[Single-Stranded DNA Library]

The single-stranded DNA library synthesized by Medclub Scientific Co. Ltd., Taiwan. Each ssDNA of the ssDNA library is a nucleotide sequence constituted by a total of 72 nucleotides. Specifically, each ssDNA includes a random sequence constituted by 40 nucleotides (represented by n), a 5'-primer region constituted by 16 nucleotides, and a 3'-primer region constituted by 16 nucleotides: 5'-ggcag-gaagacaaaca-[n]40-tggtctgtggtgctgt-3' (SEQ ID NO: 6), wherein n represents a nucleotide selected from adenine (a), thymine (t), cytosine (c), and guanine (g). In this embodiment, the 5'-primer region and the 3'-primer region are respectively designed to be nucleotide sequences recognizable by Super-Therm Gold DNA polymerase (Bertec Enterprise Co. Ltd., Taiwan) for performing a polymerase chain reaction (PCR).

A suitable amount of the ssDNA library is then dissolved in deionized water to obtain a 100 µM ssDNA library stock solution for use.

[Integrated Microfluidic Chip]

The integrated microfluidic chip of this embodiment typically includes a reaction tank, a storage tank, a fluidic control module, valves, and microfluidic channels. In this embodiment, the fluidic control module includes channels, air chambers, and pneumatic valves, wherein positive or negative pressure is generated by controlling the air chambers so as to open or close the pneumatic valves and to control the fluid flow. The above integrated microfluidic chip is used to automatically perform SELEX so as to isolate an aptamer that possesses binding specificity to ovarian cancer.

[Procedure of SELEX Selection of Aptamer Using Integrated Microfluidic System]

Figure 1:
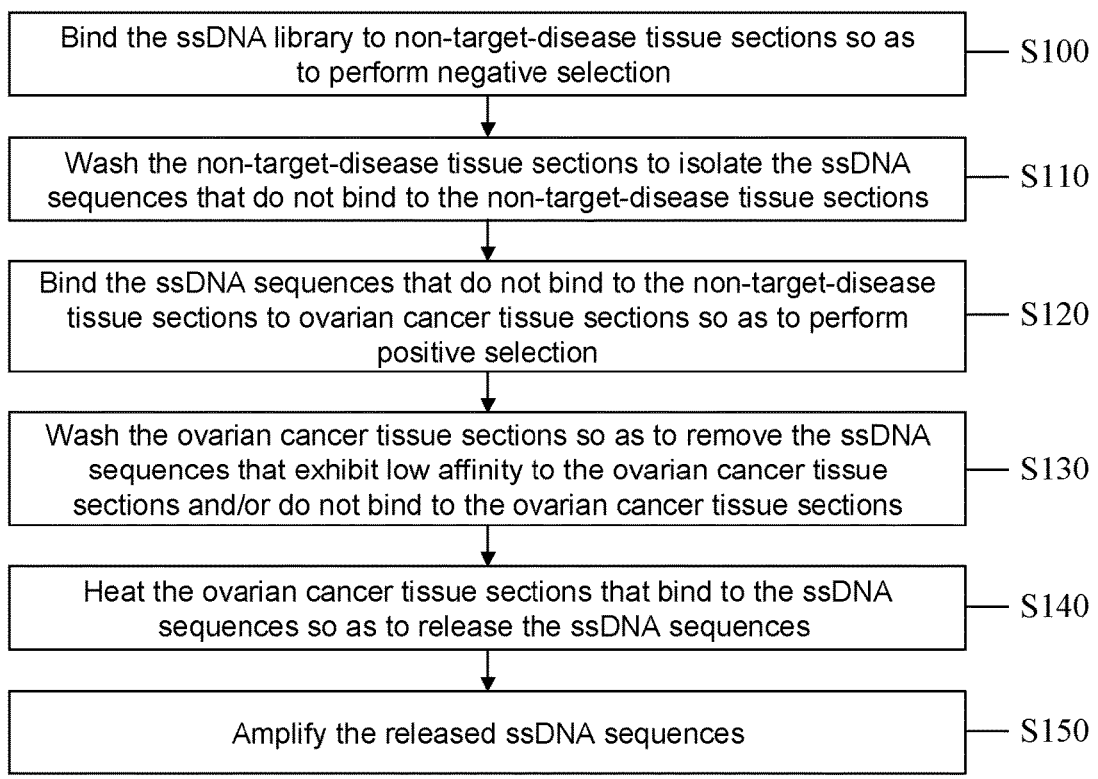
FIG. 1 is a flow chart showing the procedure of selecting an aptamer that possesses binding specificity to ovarian cancer according to an embodiment of the invention.

FIG. 1 is a flow chart showing the procedure of selecting an aptamer that possesses binding specificity to ovarian cancer according to an embodiment of the invention.

Please refer to FIG. 1, and the procedure of selecting the aptamer is provided in detail as follows:

First, the step S100 is carried out: bind the ssDNA library to non-target-disease tissue sections so as to perform negative selection. Specifically, the ssDNA library is provided to the reaction tank in which the non-target-disease tissue sections are placed, so that the ssDNA library is mixed with the non-target-disease tissue sections. In this embodiment, the non-target-disease tissue sections are, for example, normal tissue sections. But the invention is not limited thereto. Any non-ovarian-cancer tissue sections may serve as the non-target-disease tissue sections of the invention. During the process in which the binding reaction between the ssDNA library and the non-target-disease tissue sections occurs, the ssDNA sequences of the ssDNA library that are specific to the non-target-disease tissue sections bind to the non-target-disease tissue sections. In this embodiment, the binding reaction lasts for, for example, 1 to 60 minutes, preferably 30 minutes.

Next, the step S110 is carried out: wash the non-target-disease tissue sections to isolate the ssDNA sequences that do not bind to the non-target-disease tissue sections. Specifically, transmit washing buffer solution to the reaction tank and wash the non-target-disease tissue sections. During the process of washing, because the ssDNA sequences that bind to the non-target-disease tissue sections remain on the non-target-disease tissue sections, the ssDNA sequences that do not bind to the non-target-disease tissue sections are isolated accordingly.

The step S120 is then carried out: bind the ssDNA sequences that do not bind to the non-target-disease tissue sections to ovarian cancer tissue sections so as to perform positive selection. Specifically, the ssDNA sequences that do not bind to the non-target-disease tissue sections are provided to the reaction tank in which the ovarian cancer tissue sections are placed, so that the ssDNA sequences that do not bind to the non-target-disease tissue sections are mixed with the ovarian cancer tissue sections. In this embodiment, the types of ovarian cancer tissues include, for example, serous carcinoma, clear cell carcinoma, mucinous carcinoma, or endometrioid carcinoma. During the process in which the binding reaction between the above ssDNA sequences and the ovarian cancer tissue sections occurs, the ssDNA sequences that possess high specificity to the ovarian cancer tissue sections bind to the ovarian cancer tissue sections. In this embodiment, the binding reaction lasts for, for example, 5 to 60 minutes, preferably 30 minutes.

Afterwards, the step S130 is carried out: wash the ovarian cancer tissue sections so as to remove the ssDNA sequences that exhibit low affinity to the ovarian cancer tissue sections and/or do not bind to the ovarian cancer tissue sections. Specifically, transmit washing buffer solution to the reaction tank and wash the ovarian cancer tissue sections. During the process of washing, because the ssDNA sequences that exhibit high binding affinity to the ovarian cancer tissue sections remain on the ovarian cancer tissue sections, the ssDNA sequences that exhibit low affinity to the ovarian cancer tissue sections and/or do not bind to the ovarian cancer tissue sections are removed accordingly. In this embodiment, only one round of washing is performed, but the invention is not limited thereto. The number of washing round may be increased depending on the need.

Then, the step S140 is carried out: heat the ovarian cancer tissue sections that bind to the ssDNA sequences so as to release the ssDNA sequences. In this embodiment, the heating temperature is, for example, 92° C. to 98° C., preferably 95° C. Since the released ssDNA sequences possess high specificity to the ovarian cancer tissue sections, these ssDNA sequences are viewed as aptamers specific to ovarian cancer.

Afterwards, the step S150 is carried out: amplify the released ssDNA sequences. In this embodiment, the method for amplifying the released ssDNA is, for example, a PCR process, wherein the released ssDNA sequences serve as templates and the 5'-primer regions and the 3'-primer regions of the ssDNA sequences serve as primers. In addition, in this embodiment, the reaction tank of the integrated microfluidic chip serves as a polymerase chain reaction tank.

In this embodiment, the PCR products obtained above undergo a plurality of rounds of selection (for example, three rounds). Specifically, the obtained PRC products are used as the ssDNA library for the next round of selection, and the steps S100 to S150 are repeated for selecting ssDNA sequences that possess even higher specificity to ovarian cancer tissue sections. After a plurality of rounds of selection, the obtained PCR products are cloned and subject to DNA sequencing so as to obtain an aptamer that possesses high specificity to ovarian cancer.

Based on the above embodiment, an aptamer A and an aptamer B that possess high specificity to ovarian cancer are selected. The entire sequence of the aptamer A is 5'-acagcaccacagaccatcaaattacggaaaatcatgacggggtggaaccgagggggtgtttgtcttcctgcc-3' (SEQ ID NO: 4), which includes 72 nucleotides in total.

The sequence of the central region of the aptamer A is 5'-tcaaattacggaaaatcatgacggggtggaaccgagggggg-3' (SEQ ID NO: 2), which includes 40 nucleotides in total.

The entire sequence of the aptamer B is 5'-acagcaccacagaccagcaaacagctctgagacgaattccatgtgaaaacattcggtgtttgtcttcctgcc-3' (SEQ ID NO: 5), which includes 72 nucleotides in total.

The sequence of the central region of the aptamer B is 5'-gcaaacagctctgagacgaattccatgtgaaaacattcgg-3' (SEQ ID NO: 3), which includes 40 nucleotides in total.

Comparing and analyzing the entire sequences of the aptamer A and the aptamer B using two biological information software (WEBLOGO [URL: http://weblogo.berkeley.edu/logo.cgi] and T-COFFEE [URL: http://tcoffee.vital-it.ch/apps/tcoffee/index.html]) is performed, the Applicant infers that the conserved central region of the 40 nucleotides as shown below is very important to an aptamer's affinity to ovarian cancer cells and/or ovarian cancer tissues:

5'-ncaaannncnnnnanncnnnnnnnnnnngaannnannngg-3' (SEQ ID NO: 1), wherein n represents a nucleotide independently selected from adenine (a), thymine (t), cytosine (c), and guanine (g).

Figure 2:
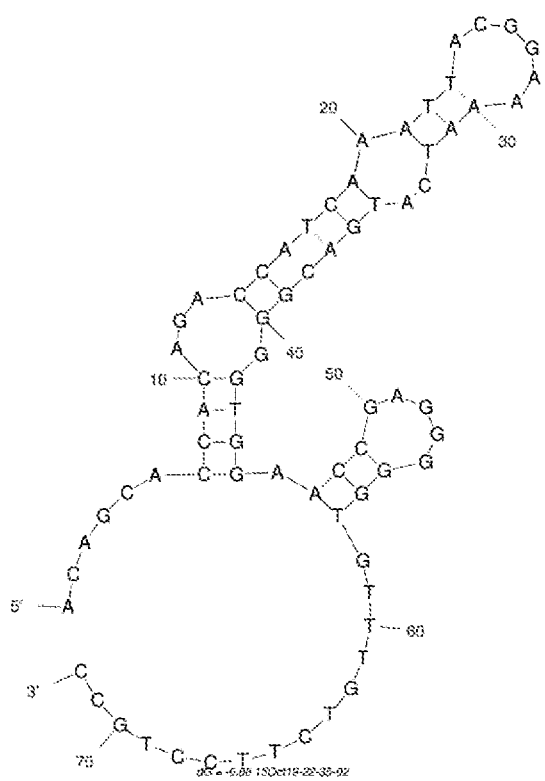
FIG. 2 shows the secondary structures of the aptamer A (SEQ ID NO: 4) and aptamer B (SEQ ID NO: 5) of the invention.
Figure 2:
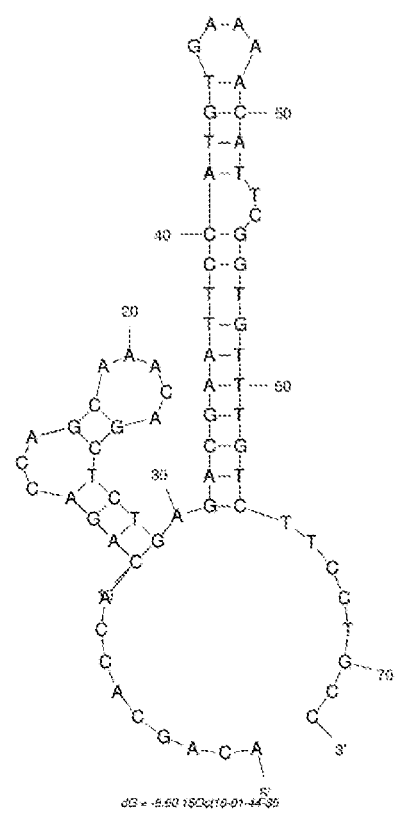

The secondary structures of the entire sequences of the aptamer A and the aptamer B (SEQ ID NO: 4 and SEQ ID NO: 5) are predicted using MFOLD software, and the result is shown in FIG. 2. In this embodiment, the aptamer A and the aptamer B, for example, each have a stem-loop secondary structure. In addition, the variations of the free energy of SEQ ID NO: 4 and of SEQ ID NO: 5 are less than −5 kcal/mol. Specifically, the variation of the free energy of SEQ ID NO: 4 is −6.88 kcal/mol, and the variation of the free energy of SEQ ID NO: 5 is −8.60 kcal/mol. The variation of the free energy is a thermodynamic property, the value of which is used to predict whether a reverse reaction is able to occur spontaneously. If the variation of the free energy presents a negative value, then the reaction is a spontaneous reaction; otherwise, a non-spontaneous reaction. In this embodiment, because the aptamer A and the aptamer B that are specific to ovarian cancer each have the variation of the free energy with a negative value, forming a three dimensional structure is thus a spontaneous reaction for the aptamer A and the aptamer B. In addition, since the variations of the free energy of the aptamers specific to ovarian cancer are small (each less than −5 kcal/mol), the formed three-dimensional structures are more stable. Therefore, the aptamers of this embodiment are suitable to serve as biomarkers for detecting ovarian cancer.

In this embodiment, a 5'-end of the aptamer is modified by any of fluorescence, a thiol group, a biotin, and an enzyme, so that the 5'-end is easily conjugated to specific matrices or has labeling characteristics such as light emission.

The invention further provides a detection method for ovarian cancer, and the detection method includes the following steps. First, at least one of the above aptamers is provided. Next, a test sample is mixed with the aptamer to make the test sample bind to the aptamer. Then, the aptamer that binds to the test sample is detected. In this embodiment, the test sample comes from, for example, ovarian cancer tissue or ovarian cancer cell. The ovarian cancer tissue is, for example, serous ovarian carcinoma tissue, clear cell ovarian carcinoma tissue, mucinous ovarian carcinoma tissue, or endometrioid ovarian carcinoma tissue. The ovarian cancer cell is, for example, OVCAR-3. In view of the fact that the aptamer of the above embodiment possesses binding specificity to ovarian cancer tissues and ovarian cancer cells, by detecting the aptamer that binds to the test sample, it is determinable whether ovarian cancer tissues or ovarian cancer cells exist in the test sample.

In the following, several experiments are disclosed to more specifically prove that the aptamer of the invention possesses high specificity to ovarian cancer. However, it will be apparent to those skilled in the art that various modifications and variations can be made to the materials and methods as delineated in the experiments below without departing from the spirit of the invention. Therefore, the following experiments should not be used to limit the scope of the invention.

Experiment 1

In this experiment, the nucleotide sequence (SEQ ID NO: 2) of the central region of the aptamer A was synthesized through chemical synthesis and served as the aptamer of this experiment (hereinafter referred to as the aptamer A-1). The 5'-end of the aptamer A-1 was then modified by carboxyfluorescein (FAM) that generated green fluorescent signals under the excitation of blue light. The modified aptamer A-1 was then respectively mixed with normal tissue sections (serving as non-target-disease tissue sections) and with a variety of different types of ovarian cancer tissue sections (serous, clear cell, mucinous, and endometrioid ovarian carcinoma tissue sections) so as to perform fluorescent dyeing. Fluorescent signals were then observed using a fluorescent microscope.

Experiment 2

In this experiment, the nucleotide sequence (SEQ ID NO: 3) of the central region of the aptamer B was synthesized through chemical synthesis and served as the aptamer of this experiment (hereinafter referred to as the aptamer B-1). The 5'-end of the aptamer B-1 was then modified by FAM. The modified aptamer B-1 was then respectively mixed with a variety of different types of ovarian cancer tissue sections (clear cell, mucinous, and endometrioid ovarian carcinoma tissue sections) so as to perform fluorescent dyeing. Fluorescent signals were then observed using a fluorescent microscope.

Figure 3:
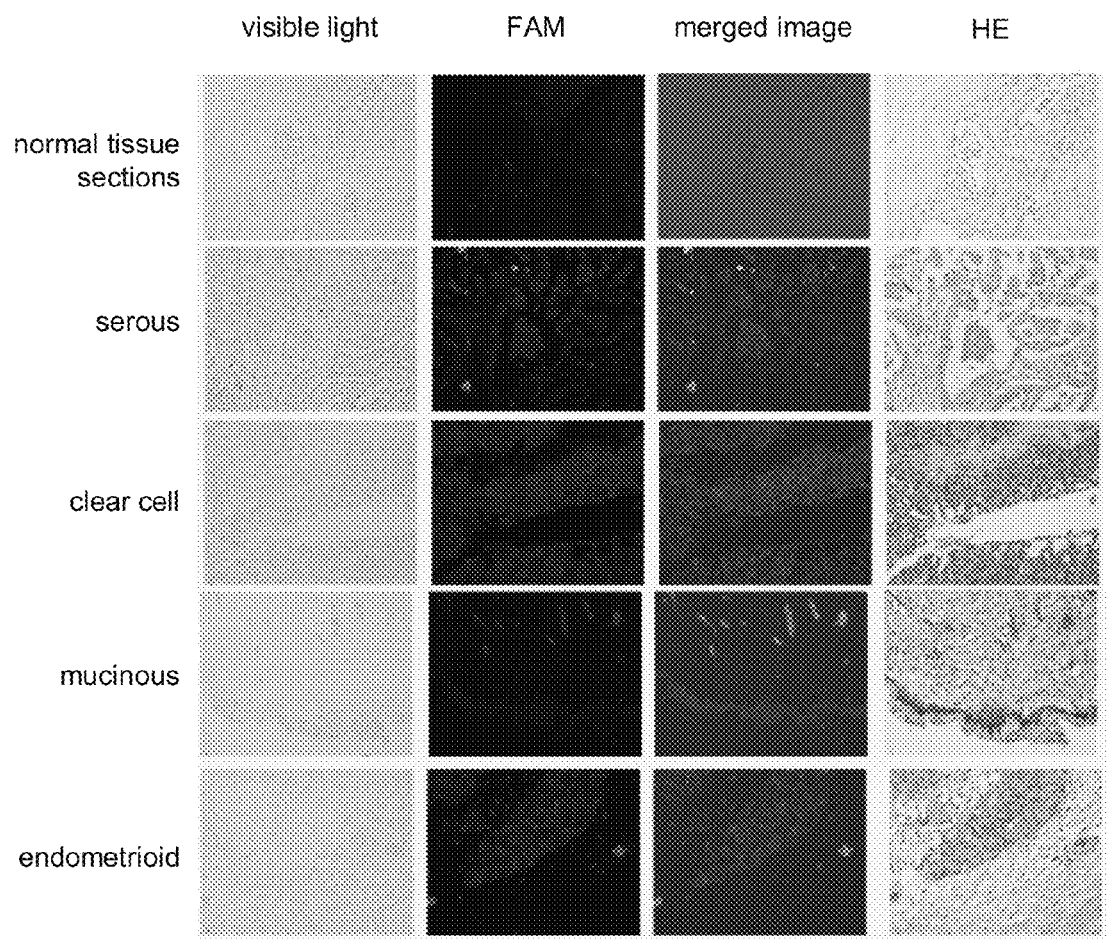
FIG. 3 is an image analysis diagram showing the fluorescent dyeing performed by the aptamer A-1 on normal tissue sections and on different types of ovarian cancer tissue sections.
Figure 4:
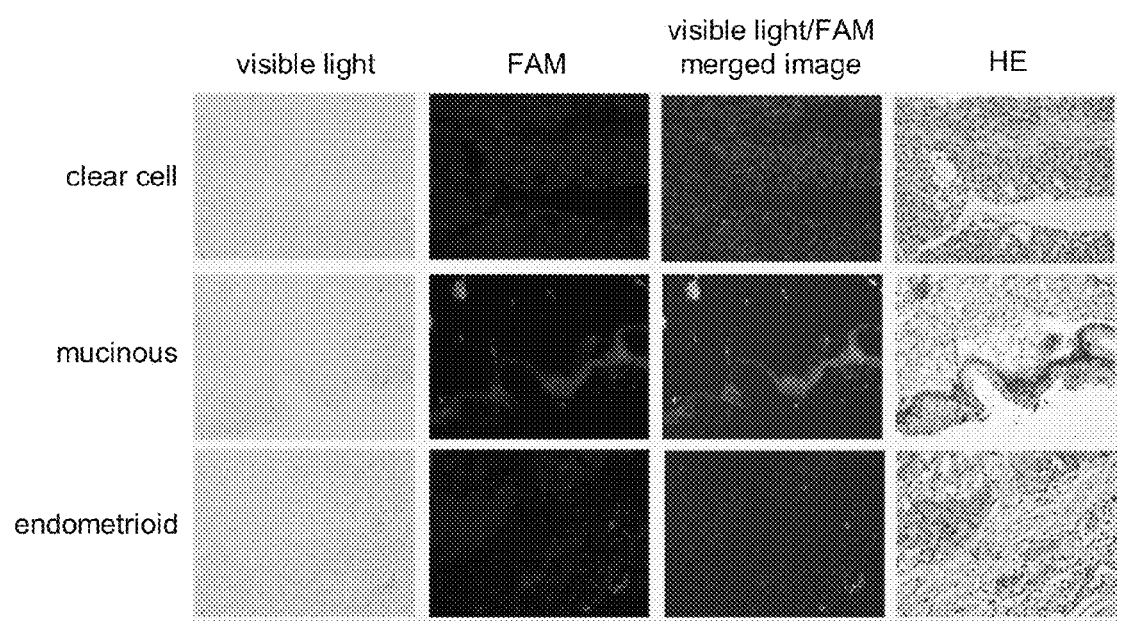
FIG. 4 is an image analysis diagram showing the fluorescent dyeing performed by the aptamer B-1 on different types of ovarian cancer tissue sections.

FIG. 3 is an image analysis diagram showing the fluorescent dyeing performed by the aptamer A-1 on normal tissue sections and on different types of ovarian cancer tissue sections. FIG. 4 is an image analysis diagram showing the fluorescent dyeing performed by the aptamer B-1 on different types of ovarian cancer tissue sections.

FIG. 3 and FIG. 4 show the visible light images, the FAM fluorescent images, and the merged images of visible light images and FAM fluorescent images after fluorescent dyeing was performed on normal tissue sections and on different types of ovarian cancer tissue sections. Under a fluorescent microscope, green fluorescent signals were only observed in the ovarian cancer tissue sections, and no green fluorescent signals were observed in the normal tissue sections. In addition, FIG. 3 and FIG. 4 further show the images after hematoxylin-eosin (HE) staining was performed on the normal tissue sections and on the different types of ovarian cancer tissue sections. The merged images of visible light images and FAM fluorescent images and the images obtained from HE staining were used to determine the specific position where the aptamer A-1 and the aptamer B-1 bound to in ovarian cancer tissue sections. In light of the above, the aptamer A-1 and the aptamer B-1 possessed binding specificity to different types of ovarian cancer tissue sections.

Experiment 3

In this experiment, the FAM-modified aptamer A-1 of Experiment 1 served as the aptamer of this experiment. The modified aptamer A-1 was respectively mixed with normal cervical epithelial cells (serving as non-target-disease cells) and with ovarian cancer cell line OVCAR-3 so as to perform fluorescent dyeing. 4',6-diamidino-2-phenylindole (DAPI) was then used to perform fluorescent dyeing on the nuclei of the aptamer A-1-processed cells, and generated blue fluorescent signals under the excitation of ultraviolet light. Fluorescent signals were then observed using a fluorescent microscope.

Figure 5:
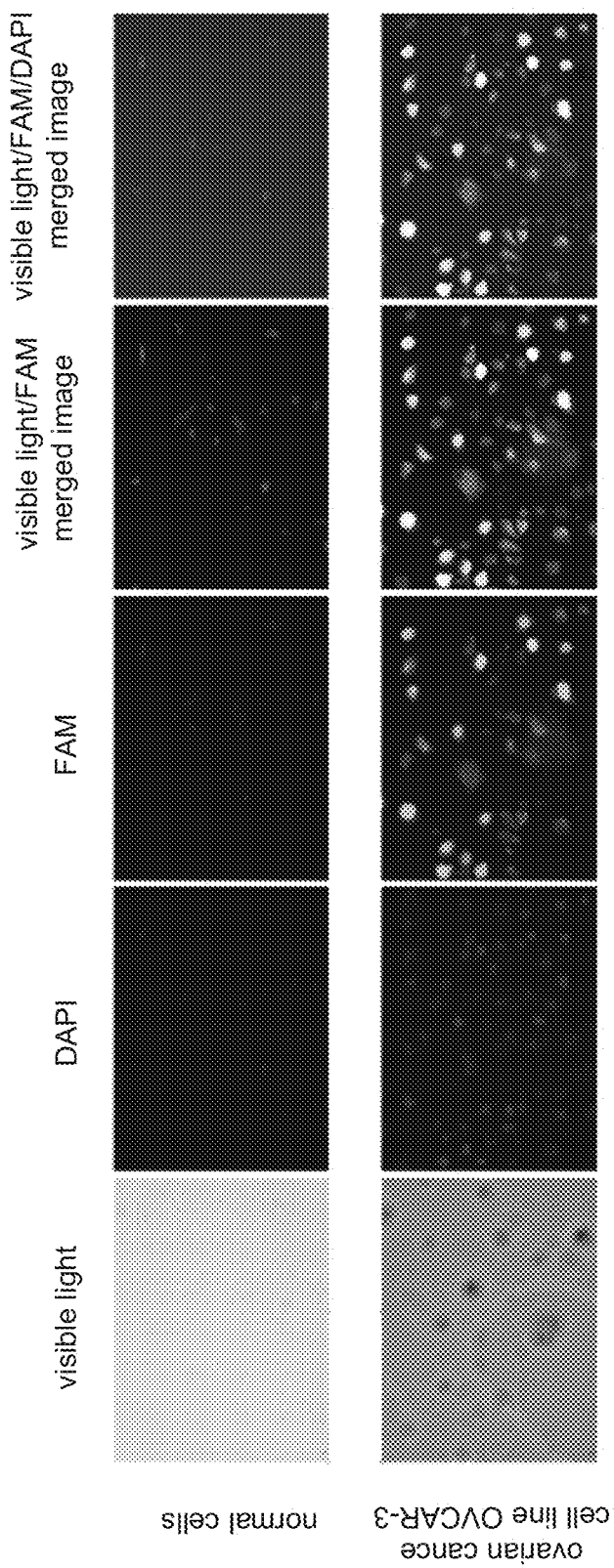
FIG. 5 is an image analysis diagram showing the fluorescent dyeing performed by the aptamer A-1 on normal cells and on ovarian cancer cell line OVCAR-3.

FIG. 5 is an image analysis diagram showing the fluorescent dyeing performed by the aptamer A-1 on normal cells and on ovarian cancer cell line OVCAR-3.

FIG. 5 shows the visible light images, the FAM fluorescent images, the DAPI fluorescent images, and the merged images of visible light images, FAM fluorescent images and DAPI fluorescent images after fluorescent dyeing was performed on normal cells and on ovarian cancer cell line OVCAR-3. Under a fluorescent microscope, green fluorescent signals were only observed in the ovarian cancer cell line OVCAR-3, and no green fluorescent signals were observed in the normal cells. In light of the above, the aptamer A-1 possessed binding specificity to ovarian cancer cells.

In summary of the above, the aptamers of the above embodiments possess high specificity and affinity to different types of ovarian cancer tissues and/or ovarian cancer cells. Therefore, a detection method for ovarian cancer using the aptamers of the above embodiments has the advantages of rapid detection, high sensitivity, and high specificity.

Although the embodiments are already disclosed as above, these embodiments should not be construed as limitations on the scope of the invention. It will be apparent to those ordinarily skilled in the art that various modifications and variations can be made to the disclosed embodiments without departing from the spirit or scope of this invention. In view of the foregoing, it is intended that the invention covers modifications and variations provided that they fall within the scope of the following claims and their equivalents.

What is claimed is:

1. An aptamer capable of binding to ovarian cancer cells, wherein the nucleotide sequence of the aptamer is SEQ ID NO: 2 or SEQ ID NO: 3.

2. The aptamer according to claim 1, wherein a variation of free energy of the aptamer is less than −5 kcal/mol.

3. The aptamer according to claim 1, wherein the aptamer has a stem-loop secondary structure.

4. The aptamer according to claim 1, wherein a 5'-end of the aptamer is conjugated to a fluorescent group, a thiol group, a biotin, or an enzyme.

5. A detection method for ovarian cancer, comprising:
providing at least one of the aptamers as recited in claim 1;
mixing a test sample with the aptamer to allow the test sample to bind to the aptamer; and
detecting the aptamer that binds to the test sample.

6. The detection method for ovarian cancer according to claim 5, wherein the test sample comprises an ovarian cancer tissue or an ovarian cancer cell.

7. The detection method for ovarian cancer according to claim 6, wherein the ovarian cancer tissue comprises a serous ovarian carcinoma tissue, a clear cell ovarian carcinoma tissue, a mucinous ovarian carcinoma tissue, or an endometrioid ovarian carcinoma tissue.

8. The detection method for ovarian cancer according to claim 6, wherein the ovarian cancer cell includes OVCAR-3.

* * * * *